United States Patent [19]

Perry

[11] Patent Number: 5,766,174
[45] Date of Patent: Jun. 16, 1998

[54] INTRAMEDULLARY BONE FIXATION DEVICE

[75] Inventor: Clayton R. Perry, St. Louis, Mo.

[73] Assignee: OrthoLogic Corporation, Phoenix, Ariz.

[21] Appl. No.: 533,905

[22] Filed: Sep. 26, 1995

[51] Int. Cl.[6] .................................................. A61B 17/56
[52] U.S. Cl. ........................... 606/62; 606/64; 606/67
[58] Field of Search ............................ 606/62, 63, 64, 606/95, 104, 99, 65, 66, 67, 68, 60, 76, 86, 96, 232; 411/488, 489, 496

[56] References Cited

U.S. PATENT DOCUMENTS

| | | | |
|---|---|---|---|
| 1,193,503 | 8/1916 | Braddock | 411/489 |
| 2,614,559 | 10/1952 | Livingston | 606/64 |
| 3,744,488 | 7/1973 | Cox | 606/64 |
| 4,040,129 | 8/1977 | Steinemann et al. | 606/76 |
| 4,355,427 | 10/1982 | Schneider | 606/62 |
| 4,503,847 | 3/1985 | Mouradian . | |
| 4,817,591 | 4/1989 | Klaue | 606/64 |
| 4,865,025 | 9/1989 | Buzzi et al. | 606/96 |
| 4,913,137 | 4/1990 | Azer et al. | 606/96 |
| 4,919,670 | 4/1990 | Dale et al. . | |
| 5,034,013 | 7/1991 | Kyle et al. | 606/62 |
| 5,112,333 | 5/1992 | Fixel . | |
| 5,263,955 | 11/1993 | Baumgart et al. | 606/63 |
| 5,318,570 | 6/1994 | Hood et al. | 606/99 |
| 5,334,192 | 8/1994 | Behrens | 606/102 |
| 5,429,640 | 7/1995 | Shuler et al. | 606/64 |
| 5,472,444 | 12/1995 | Huebner et al. | 606/62 |
| 5,496,289 | 3/1996 | Wenstrom, Jr. | 606/232 |
| 5,505,734 | 4/1996 | Caniggia et al. | 606/63 |

OTHER PUBLICATIONS

Sampson Corp., Fluted Intramedullary Rod System, Mar. 1974.

*Primary Examiner*—Michael Buiz
*Assistant Examiner*—Julian W. Woo
*Attorney, Agent, or Firm*—Dykema Gossett PLLC

[57] ABSTRACT

An intramedullary rod having a cylindrical proximal portion and a rectangular distal portion has a tapering blade-like portion. The intramedullary rod provides rotational stability and resistance to axial migration. Proximal and distal transfixation holes may be provided in the intramedullary rod.

9 Claims, 2 Drawing Sheets

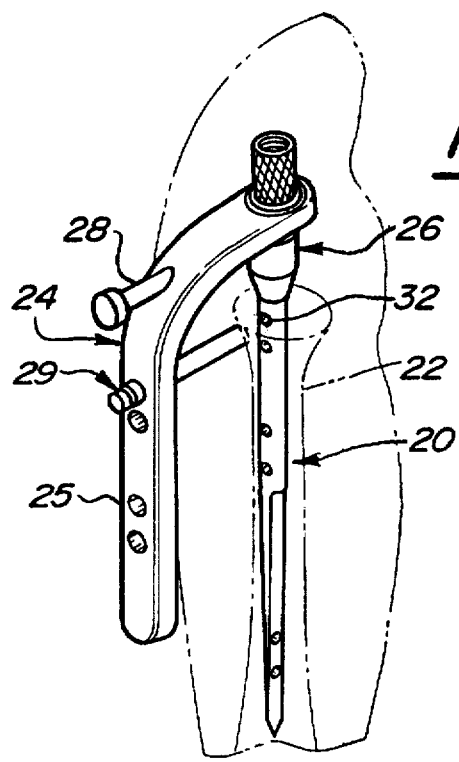
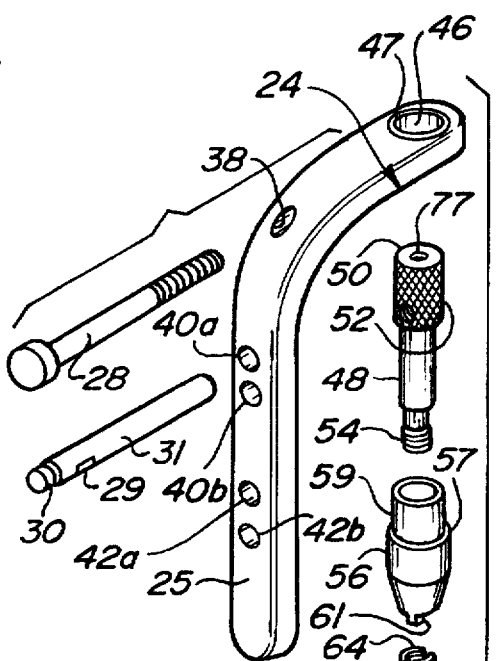
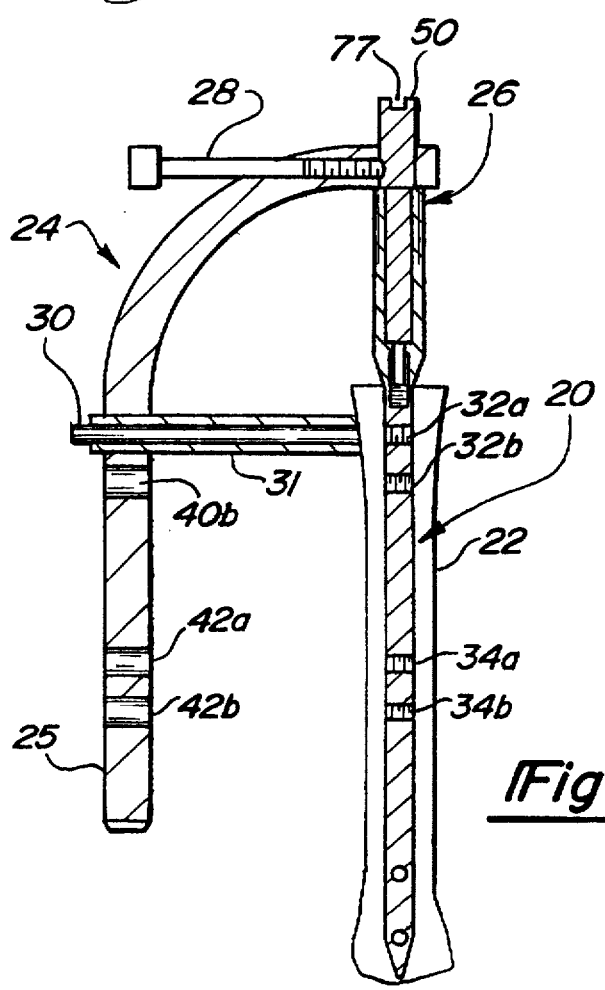

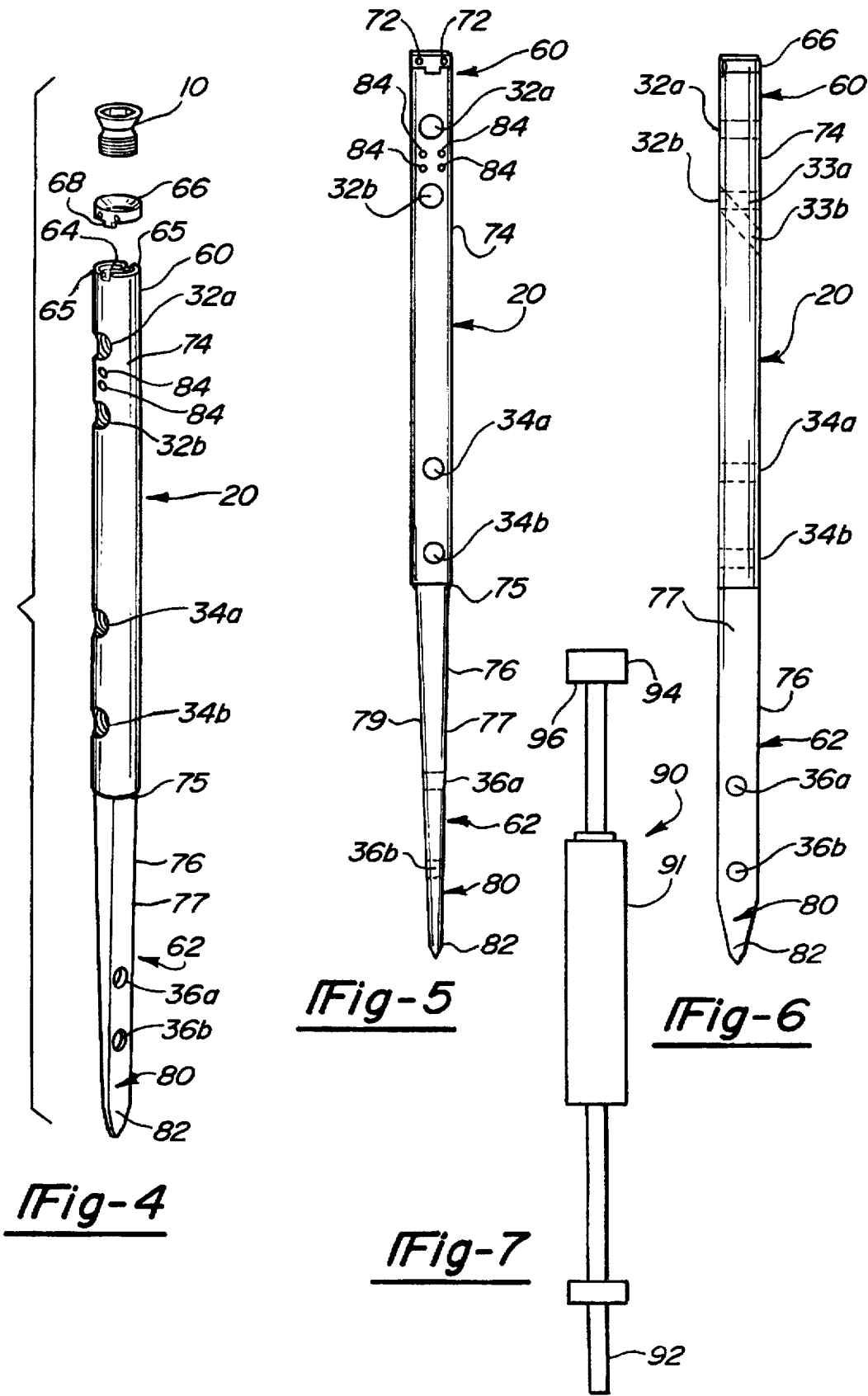

INTRAMEDULLARY BONE FIXATION DEVICE

TECHNICAL FIELD

The present invention relates generally to devices used for stabilizing bone fractures. More specifically, the present invention relates to intramedullary nails.

BACKGROUND OF THE INVENTION

Fractures of long bones, such as the humerus, are often successfully treated through the use of an intramedullary fixation device in the form of a rod or nail. These fixation devices are useful not only with transverse simple fractures but also with comminuted and segmental fractures. In essence, intramedullary rods stabilize fractures by acting as an internal splint. Early non-fixed rods were not always adequately secured to the bone, particularly with comminuted fractures. In some instances, these non-fixed rods would become loose. A section of the bone could then rotate around the nail or shift axially, causing a rotational displacement about the fracture line, a gap or other discontinuity. In order to provide rotational stability to the fractured bone, many conventional intramedullary nails now have transverse holes for receiving a fastener such as a screw. The transverse holes are typically located at opposed ends of the nail, which for convenience are referred to as the proximal end and the distal end. Nails having these transfixation holes are often referred to as "locking nails." By securing the nail to the bone through the use of transfixation screws, rotation of the bone relative to the nail is prevented. It is also known that the use of both proximal and distal locking reduces axial displacement of bone along the rod and provides additional torsional rigidity.

Intramedullary nails are inserted in the bone using well known techniques. In the case of the humerus, sufficient tissue is removed to allow the nail to be inserted into the intramedullary canal. Various alignment devices are available for aligning the proximal end of the nail so that the surgeon can locate and align the transfixation holes. With respect to the distal end of the nail, however, it is much more difficult to align the transfixation holes. Typically, the holes in the distal must be located by x-ray imaging using an image intensifier; several attempts may be required before transfixation is successful. Thus, the transfixation of the distal ends of intramedullary nails is usually a difficult procedure.

It will be appreciated by those skilled in the art that the intramedullary canal of the humerus does not have a uniform cross section along its entire length. Many prior art intramedullary nails are not well adapted for use in bones having these nonuniform cavities. In addition, the relative placement of the transfixation holes of known prior art intramedullary nails does not readily facilitate the use of a C-arm, X-ray machine to locate holes at the distal end. Still further, known prior art intramedullary nails do not provide convenient means for attaching bone fragments or soft tissue to the nail. Accordingly, there is a need for an intramedullary nail which addresses these needs.

It is an object of the invention to provide an intramedullary nail which is specifically adapted to conform to the non-uniform cross-sectional areas of certain long-bone intramedullary canals.

It is a further object of the invention to provide an intramedullary nail that provides good anti-rotational and anti-axial stabilization of bone segments, often without the use of distal transfixation screws.

It is still a further object of the invention to provides an intramedullary nail having distal transfixation holes which may be easily located using a C-arm.

It is still a further object of the invention to provide an intramedullary nail having means by which small fragments of bone or soft tissue can be attached to the nail at certain locations.

It is still a further object of the invention to provide an intramedullary nail which has a plurality of transfixation sites that allow the nail to be more readily adapted to various types of fractures.

SUMMARY OF THE INVENTION

The present invention provides an intramedullary nail for stabilizing proximal, middle and distal fractures of long bones. In one aspect the intramedullary nail of the present invention has a cylindrical proximal portion and a distal flat portion. The cylindrical proximal portion has a preselected radius and an anvil receiving surface at one end. The distal flat portion is tapered and has at least one flat surface which terminates in an arcuate tissue penetrating tip at one end.

In still another aspect the distal flat portion of the intramedullary nail of the present invention is a blade having opposed flat sides. The anvil-receiving surface of the cylindrical proximal portion has a threaded aperture for receiving a threaded portion of the anvil.

In still another aspect, the intramedullary nail of the present invention has transverse holes for receiving transfixation screws at two axially-displaced locations along the cylindrical proximal portion and transverse fixation holes in the flat distal portion.

In still another aspect, the intramedullary nail of the present invention has a plurality of suture holes that allow tissue and tuberosities to be sutured to a portion of the nail.

In still another aspect the intramedullary nail of the present invention includes an end cap attached to the anvil-receiving end of said cylindrical proximal portion.

In still another aspect, the intramedullary nail of the present invention provides a bidirectional transfixation hole for securing bone fragments.

These and other features and advantages of the invention will become apparent in connection with the detailed description of the invention with reference to the drawings.

BRIEF DESCRIPTION OF THE DRAWINGS

FIG. 1 is a perspective view of the intramedullary nail of the present invention attached to an alignment tower.

FIG. 2 is an exploded view of the apparatus shown in FIG. 1.

FIG. 3 is a cross-sectional elevational view of the apparatus shown in FIGS. 1 and 2.

FIG. 4 is a perspective view of the intramedullary nail of FIG. 1.

FIG. 5 is a front view of the intramedullary nail of FIG. 1.

FIG. 6 is a side view of the intramedullary nail of FIG. 1.

FIG. 7 is a front elevational view of an extraction device used for removing the intramedullary nail of the present invention.

DETAILED DESCRIPTION OF THE PREFERRED EMBODIMENTS THE INVENTION

Referring now to FIGS. 1 and 2 of the drawings, intramedullary nail or fixation rod 20 is shown implanted in humerus 22 to stabilize a fracture (not shown). Alignment tower 24 has side bar 25 and is attached to intramedullary nail 20 via anvil assembly 26. Locating screw 28 extends through locating screw bore 38, the latter of which is best shown in FIG. 2 of the drawings. Nested drill guide and screw sleeve assembly 29 extends through guide hole 40A of side arm 25. Nested drill guide and screw sleeve assembly 29 is comprised of drill guide 30 and screw locator sleeve 31. Nail 20 has a plurality of transfixation holes for interlocking nail 20 with humerus 22. More specifically, proximal transfixation holes 32a and 32b, intramedullary or bone transfixation holes 34a and 34b and distal transfixation holes 36a and 36b are preferably provided. Thus, it will be appreciated that transfixation holes are provided proximally, midlength and distally for transfixation. This feature will be explained more fully hereinafter. Proximal transfixation holes 32a and 32b and intermediary transfixation holes 34a and 46 are accessed, respectively, through the use of guide holes 40a, 40b, 42a and 42b.

Alignment tower 24 has anvil hole 46 into which anvil assembly 26 is received. Anvil shaft portion 48 has anvil impact end 50 which receives blows from a mallet during insertion. Threaded tip 54 is provided in order to secure anvil 26 to nail 20. Anvil cone portion 56 having shoulder 57 is threaded onto and beyond the threaded tip 54 of anvil shaft 48 and is then held loosely thereon. Once threaded tip 54 is screwed into anvil 20, anvil cone portion 56 is secured on shaft 48. Alignment tower 24 engages shoulder 57 at anvil hole 46. Anvil assembly 26 includes locating indent or indentation 59 which is simply a small point indentation. Anvil 26 is provided with opposed tabs or tangs, one of which is shown as tab 61.

As beat shown in FIG. 3 of the drawings, through the use of alignment tower 24 and locating screw 28, intramedullary nail 20 is indexed such that transfixation holes 40a and 40b are in alignment with proximal transfixational holes 32a and 32b of nail 20. Guide holes 42a and 42b are then in alignment with intramedullary transfixation holes 34a and 34b. In a manner to be described more fully hereinafter, this alignment allows nested drill guide and screw assembly 29 to be used to locate the transfixation holes.

Referring now to FIGS. 4, 5 and 6 of the drawings, intramedullary nail 20 is seen having proximal end 60 and distal end 80. Proximal end 60 has a shallow threaded portion 64 that includes a pair of opposed notches 65. Nail cap 66 is shown which includes nail cap tabs 68 (one shown in FIGS. 4 and 5) which insert in notches or slots 65 in mating relationship. As shown best in FIG. 5, nail cap 66 has a pair of suture holes that pass therethrough.

Nail cap screw 70 may also have transverse holes which align with nail cap suture holes 72. In other words, nail cap suture holes 72 would then pass completely through the nail cap assembly when secured by screw 70.

Nail cap suture holes 72 as well as nail suture holes 84 are provided for holding sutures during attachment of soft tissues and tuberosities.

Nail cap 66 is optionally provided to protect threaded portion 64 of nail 20 from tissue ingrowth. Intramedullary nail 20 has proximal cylindrical section 74 and distal rectangular section or tapered blade 76.

The cross-sectional diameter of proximal cylindrical section 74 is most preferably between about 8 to 12 mm and the overall length of nail 20 is preferably from about 195 to 315 mm. Distal section 76 has at least one flat surface 77 and more preferably opposed flat surfaces 77 and 79. The distal end of distal section 76 comprises nail tip 80 having triangular tissue penetrating point 82. Referring to FIGS. 4, 5 and 6, it will be seen that distal section 76 and the most preferred embodiment, and as best shown in FIG. 5, is tapered preferably the entire length of distal section 76. Where tapered blade 76 is flat, it has a thickness of from about 0.24 inches to 0.26 inches converging to a thickness of from about 0.1 inches to 0.12 inches at tip 80. By providing rectangular section 76 at the distal end of nail 20, greater resistance to torsion is achieved in unreamed cavities. Accordingly, in some instances, the change in section and the taper of nail 20 provide enough rotational stability and resistance to axial migration such that proximal and/or distal transfixation through the use of transfixation may not be necessary.

Proximal cylindrical section 74 is provided with a plurality of transfixation holes. More specifically, proximal transfixation holes 32a and 32b extend through proximal cylindrical section 74. Most preferably, as best shown in FIG. 6 of the drawings, transfixation hole 32b has a main (perpendicular) passage 33a and an applied passage 33b. Passage 33b may be used to better affix bone fragments, where an angle to the direction of the fixation screw is desirable. Passage 33b is preferably at an angle of 10–60 degrees and most preferably about 30 degrees to passage 33a. The entrance to hole 32b may be slightly enlarged (elliptical) for this purpose. Proximal transfixation holes 32a and 32b, as well as intermediary holes 34a and 34b and distal transfixation holes 36a and 36b, receive transfixation screws (not shown) in the manner to be described hereinafter. Similarly, intermediary transfixation holes 34a and 34b are shown extending through cylindrical section 74 distal to proximal transfixation holes 32a and 32b. Distal transfixation holes 36a and 36b extend through distal section 76.

Referring again to FIGS. 4, 5 and 6, it will be appreciated that intramedullary nail or rod 20 is cylindrical proximally and rectangular distally. Distal flat section 76 provides anti-rotational stability even without transfixation at distal transfixation holes 36a and 36b. In addition, distal transfixation holes 36a and 36b are rotated 90° from the axes defined by proximal transfixation holes 32a and 32b and intermediary transfixation holes 34a and 34b. Therefore, distal hole targeting is more readily achieved through the use of a C arm since distal transfixation holes 36a and 36B are oriented in the anterior-posterior direction.

A number of materials may be used to fabricate intramedullary nail 20, however a titanium alloy, preferably 6A1–4 v Ti alloy conforming to ASTM standard F-136-92, as most preferred. The cross-sectional diameter of proximal cylindrical section 74 can be selected to optimize proximal intramedullary canal filling. In addition, the overall length of nail 20 as well as the relative lengths of proximal cylindrical section 74 and distal section 76 are chosen to correspond with the characteristics of the bone geometry. In most applications, the length of distal section 76 between the end of triangular point 82 and the end 75 of proximal cylindrical section 74 will be from about 10% to 30% less than the length of proximal cylindrical section 74. In other words, distal portion 76 will be between about 70% and 90% of the length of proximal cylindrical section 74. In other applications, it may be preferable to make distal portion 76 longer than proximal cylindrical section 74. In some instances, distal portion 76 is from about 10–30% longer than proximal cylindrical portion 74.

Referring again to FIG. 2 of the drawings, alignment tower 24 is most preferably fabricated from a high temperature thermoplastic such as polyetherimide which can withstand repeated steam and gamma sterilization. Anvil hole 46 preferably has a stainless steel insert 47 which receives anvil shaft portion 48. Similarly, metal inserts (not shown) may be used to align guide holes 40a, 40b, 42a, 42b and locating screw bore 38. Screw bore 38 is provided for locating screw 28 to pass therethrough. Locating screw 28 is received in indent 59 of anvil assembly 26 and serves to index nail 20 in position. As stated, alignment tower 24 abuts shoulder 57 of anvil assembly 26. Anvil assembly 26 is preferably manufactured from stainless steel, preferably 17-4 PH stainless steel.

Referring now to FIG. 7 of the drawings, extraction device 90 is shown generally having end 92 that is inserted into threaded portion 64 of nail 20. Head 94 provides a surface 96 which is struck by a mallet or preferably by slide hammer 91 to extract nail 20 from humerus 22.

Extraction device 90 is preferably used to better align nail 20 during insertion. That is, end 92 can be screwed into extraction hole 77 (which is threaded) of anvil assembly 26. Extraction device 90 can then be struck (with slide hammer 91, which slides up and down on the shaft of extraction device 90) upwardly to loosen nail 20 to reposition it. Extraction device 90 can also be used in this manner as a driver, i.e., it can be used to further drive nail 20 into position.

Intramedullary nail 20 is used in the following manner. X-rays of the fractured bone, typically a long bone and most preferably the humerus, are viewed to determine the appropriate size of nail 20 to be utilized. The fracture is then reduced to achieve an anatomical alignment by conventional means. Nail cap 66 is removed from nail 20 and anvil assembly 26 is attached to nail 20 at threaded portion 64. Anvil assembly 26 must be firmly seated on nail 20.

In the case of a fracture of the humerus, a small incision that starts at the antero-lateral aspect of the acromion extending parallel to the fibers of the deltoid muscle is made. The cortex of the bone is perforated at or lateral to the edge of the articular surface of the humerus, posterior to the bicipital groove. A guide wire is then inserted and passed approximately half way down the humerus. Using a cannulated drill or reamer the canal is reamed to a predetermined depth, for example about 70 mm. It is to be understood that in some applications, it may not be necessary to ream the bone prior to insertion of nail 20 and that nail tip 80 and the tapered nature of distal rectangular section 76 allow nail 20 to penetrate the bone tissue.

Nail 20 is then threaded onto anvil assembly 26. Tabs 61 fit into notches 65 which align indent 54 with holes 32a and 32b. Nail 20 is then inserted using a mallet to strike anvil assembly 26. Proximal transfixation holes 32a and 32b and intermediary transfixion holes 34a and 34b are oriented in the lateral direction. Accordingly, distal transfixion holes 36A and 36b are then oriented in the A–P direction.

Alignment tower 24 is then placed on anvil assembly 26 with a portion of anvil shaft 48 projecting through anvil hole 46 and such that tower 24 abuts shoulder 57. Locating screw 28 is rotated to extend it into indent 59. This procedure properly aligns transfixation holes 32a and 32b and 34a and 34b of nail 20 with guide holes 40a and 40b and 42a and 42b respectfully.

Nested drill guide sleeves 29 are inserted in each guide hole 40a, 40b, 42a and 42b, in abutment with the surface of the bone as shown best in FIG. 3. Using a surgical drill, the bit of a surgical drill is then passed through drill guide 30 to form a hole extending from the surface of bone 22 to the first transfixion hole 32a as shown in FIG. 3. The bit is then withdrawn and drill guide 30 removed, leaving screw locator sleeve 31 in position. A transfixation screw (not shown) is then inserted through screw locator sleeve 31 whereupon it is passes through proximal transfixation hole 32a such that the head of the screw is on the external surface of bone 22 and the distal threaded end extends through hole 32a and is screwed into cortical bone on the other side. If desired, passage 33b can be used to place a transfixation screw at an angle. Of course the alignment guides cannot be used for this purpose. This procedure may be repeated for the remaining transfixation holes 32b, 34a and 34b. As will be appreciated by those skilled in the art, the transfixation screws are cancellous or cortical screws.

If required for greater stability, transfixation screws may be used to secure distal section 76, via distal transfixation holes 36A and 36b through the use of a C-arm (i.e. by x-ray targeting of the transfixion holes and drilling). It will be appreciated that the configuration of nail 20 in the present invention will in many instances provide sufficient rotational stability such that distal transfixation may not necessary. The alignment tower and anvil are then removed and the incision is closed.

Thus, it is apparent that there has been provided in accordance with the invention a method and apparatus that fully satisfies the objectives, aims and advantages set forth above. While the invention has been described in connection with specific embodiments thereof, it is evident that many alternatives, modifications, and variations will be apparent to those skilled in the art in light of the foregoing description. Accordingly, it is intended to embrace all such alternatives, modifications and variations that fall within the spirit and broad scope of the appended claims.

What is claimed is:

1. An intramedullary nail for insertion into bone tissue, comprising:

a single straight solid intramedullary nail metal body having a proximal portion and a distal portion, said distal portion terminating in a tip:

said tip having an arcuate terminus;

said proximal portion comprising a cylindrical shaft having an end, said end being threaded to receive a threaded anvil;

said distal portion comprising a rectangular section having parallel sides and opposed flat faces, said rectangular portion being disposed between said cylindrical portion and said tip;

said rectangular section of said distal portion of said nail being adapted to provide torsional stability to said intramedullary nail in said bone tissue:

wherein said opposed flat surfaces which converge toward said tip and said tip form a tapered blade:

said cylindrical shaft having at least one transfixation hole defined therein.

2. The intramedullary nail recited in claim 1, wherein a cap is attached to said end of said cylindrical shaft.

3. The intramedullary nail recited in claim 1, wherein said proximal portion is longer than said distal portion.

4. The intramedullary nail recited in claim 1, wherein said proximal portion and said distal portion are of approximate equal length.

5. The intramedullary nail recited in claim 1, wherein said distal portion defines at least one transverse hole for receiving a transfixing screw.

6. The intramedullary nail recited in claim 1, wherein said proximal portion defines at least one transverse suture hole that extends through said proximal portion.

7. The intramedullary nail recited in claim 1, wherein said metal body is a titanium alloy machined to shape.

8. The intramedullary nail recited in claim 1, wherein said proximal portion defines at least one hole along a first axis to receive a transfixing screw, said distal portion defines at least one hole along a second axis to receive a transfixing screw, and wherein said first axis is perpendicular to said second axis.

9. The intramedullary nail recited in claim 1, wherein said distal portion is longer than said cylindrical portion.

* * * * *